(12) United States Patent
Zeng et al.

(10) Patent No.: US 12,239,879 B1
(45) Date of Patent: Mar. 4, 2025

(54) UPPER LIMB REHABILITATION DEVICE AND METHOD OF ITS APPLICATION FOR SARCOPENIA

(71) Applicant: Beijing Union Medical College Hospital of the Chinese Academy of Medical Sciences, Beijing (CN)

(72) Inventors: Ping Zeng, Beijing (CN); Yan Qin, Beijing (CN); Wen Zhang, Beijing (CN); Qi Zhao, Beijing (CN)

(73) Assignee: Beijing Union Medical College Hospital of the Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 18/806,755

(22) Filed: Aug. 16, 2024

(30) Foreign Application Priority Data

Aug. 31, 2023 (CN) .......................... 202311110227.7

(51) Int. Cl.
| | | |
|---|---|---|
| *A63B 23/16* | (2006.01) |
| *A61B 17/132* | (2006.01) |
| *A61H 39/04* | (2006.01) |
| *A63B 21/02* | (2006.01) |
| *A63B 23/035* | (2006.01) |

(52) U.S. Cl.
CPC .......... *A63B 23/16* (2013.01); *A61B 17/1325* (2013.01); *A61H 39/04* (2013.01); *A63B 21/028* (2013.01); *A63B 23/03525* (2013.01); *A61H 2201/0153* (2013.01); *A61H 2201/105* (2013.01); *A61H 2201/1695* (2013.01); *A61H 2205/065* (2013.01)

(58) Field of Classification Search
CPC . A63B 23/16; A63B 21/028; A63B 23/03525; A61H 39/04; A61H 2201/0153; A61H 2201/105; A61H 2201/1695; A61H 2205/065; A61B 17/1325
See application file for complete search history.

(56) References Cited

U.S. PATENT DOCUMENTS

| | | | |
|---|---|---|---|
| 2003/0010744 A1* | 1/2003 | Ma ........................ | B65D 1/0223 215/382 |
| 2003/0032996 A1* | 2/2003 | Hallman ................... | A61F 7/10 607/108 |

(Continued)

FOREIGN PATENT DOCUMENTS

| | | |
|---|---|---|
| CN | 209422872 U | 9/2019 |
| CN | 209450902 U | 10/2019 |

(Continued)

*Primary Examiner* — Jing Rui Ou
(74) *Attorney, Agent, or Firm* — Bayramoglu Law Offices LLC

(57) ABSTRACT

An upper limb rehabilitation device for sarcopenia and its application method are provided, which is less likely to cause harm to patients, more suitable for people with weaker strength, can encourage to exercise combined with fun, and can significantly improve the upper limb muscle function of sarcopenia patients. The upper limb rehabilitation device for sarcopenia includes an outer surface, a filling material, and a keel. The shape of the outer surface is shuttle shaped, the keel is made of rubber material, the filling material is between the keel and the outer surface, including sponge particles and wormwood particles, and hand acupoint protrusion particles are set on the outer surface.

4 Claims, 1 Drawing Sheet

(56) References Cited

U.S. PATENT DOCUMENTS

| | | | |
|---|---|---|---|
| 2003/0223844 A1 | 12/2003 | Schiele et al. | |
| 2004/0186400 A1* | 9/2004 | Thomas | A61H 7/001 601/135 |
| 2004/0249324 A1* | 12/2004 | Louis | A61H 7/003 601/135 |
| 2007/0232970 A1* | 10/2007 | Kyoji | A63B 57/20 601/118 |
| 2008/0027364 A1* | 1/2008 | Moutray | A61H 7/001 601/134 |

FOREIGN PATENT DOCUMENTS

| | | |
|---|---|---|
| CN | 211610619 U | 10/2020 |
| CN | 115025462 A | 9/2022 |
| JP | 2006288529 A | 10/2006 |

\* cited by examiner

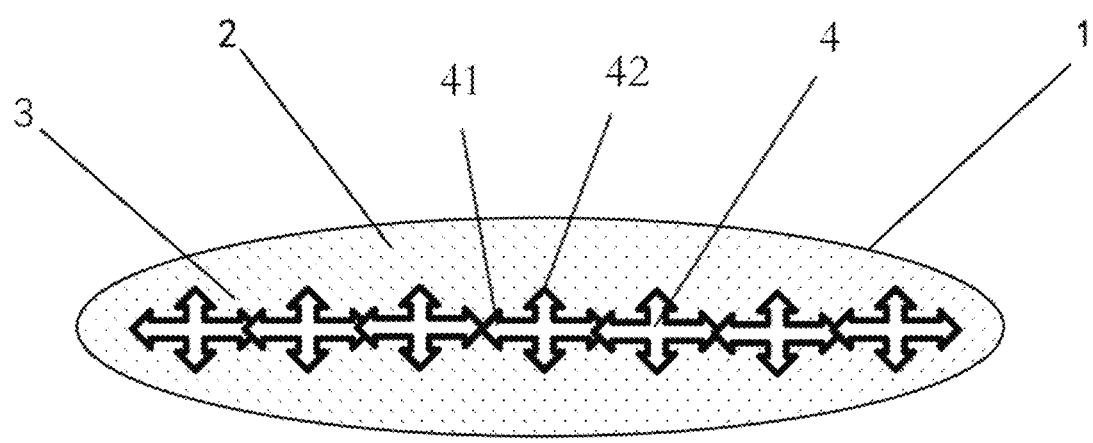

UPPER LIMB REHABILITATION DEVICE AND METHOD OF ITS APPLICATION FOR SARCOPENIA

CROSS-REFERENCE TO THE RELATED APPLICATIONS

This application is based upon and claims priority to Chinese Patent Application No. 202311110227.7, filed on Aug. 31, 2023, the entire contents of which are incorporated herein by reference.

TECHNICAL FIELD

The present invention relates to the technical field of rehabilitation care equipment, and particularly relates to an upper limb rehabilitation device for sarcopenia.

BACKGROUND

Frailty is one of the most clinically challenging geriatric syndromes, characterized by an imbalance in physiological homeostasis and function centered around sarcopenia. Sarcopenia is a progressive decline in skeletal muscle mass and function that occurs with age, accounting for over 10% in individuals aged 60 and above, and over 30% in those aged 80 and above. Sarcopenia not only seriously reduces the quality of life of the elderly population, but also increases the burden of elderly care on families and society.

At present equipments for upper limb muscle function exercise and handheld grip strength improvement are mostly grip rings and grip balls. Grip rings are widely used and use harder rubber materials, requiring a greater grip strength to achieve the exercise effect. They are mostly used for people with slightly decreased function, and it is difficult for patients with weaker strength to cooperate. And the texture is too hard with poor hand feel. It is easy to cause fatigue and frustration, therefore adherence to usage is poor. Sponge grip balls can improve the above problems to a certain extent, but their relatively single function makes them less attractive to aging/bedridden patients and adherence to usage is average.

SUMMARY

In order to overcome the defects of the prior art, the technical problem to be solved by the invention is to provide an upper limb rehabilitation device for sarcopenia, which is less likely to cause harm to patients, more suitable for people with weaker strength, can encourage to exercise combined with fun, and can significantly improve the upper limb muscle function of sarcopenia patients.

The technical scheme of the invention is as follows. The upper limb rehabilitation device for sarcopenia includes an outer surface 1, filling material 2, and a keel 3.

The shape of the outer surface is shuttle shaped, the keel is made of rubber material, the filling material is between the keel and the outer surface, including sponge particles and wormwood particles, and hand acupoint protrusion particles are set on the outer surface.

In the present invention the shape of the outer surface is shuttle shaped, the keel is made of rubber material, and the filling material is between the keel and the outer surface, including sponge particles and wormwood particles, which is less likely to cause harm to patients, more suitable for people with weaker strength, can encourage to exercise combined with fun, and can significantly improve the upper limb muscle function of sarcopenia patients. At the same time, it can also have a massage effect on hand acupoints, and because it contains the Chinese herbal medicine of wormwood, it can promote blood circulation, remove blood stasis, dispel dampness and help sleep.

An application method for the upper limb rehabilitation device for sarcopenia is also provided, which includes the following steps:
(1) placing two hands at the location of the hand acupoint protrusion particles;
(2) grasping the upper limb rehabilitation device for sarcopenia hard with the hands, so that the keel is close to the hand acupoint protrusion particles;
(3) releasing the hands and restoring the upper limb rehabilitation device for sarcopenia to its original state under the action of sponge particles;
(4) repeating step (1)-(3) repeatedly until a rehabilitation plan is reached.

BRIEF DESCRIPTION OF THE DRAWINGS

FIGURE is a structural schematic diagram of the upper limb rehabilitation device for sarcopenia according to the present invention.

DETAILED DESCRIPTION OF THE EMBODIMENTS

In order to make the purpose, technical solution, and advantages of the present invention clearer and more understandable, the following will provide further detailed explanations of the present invention in conjunction with the drawings and specific embodiments. It should be understood that the specific embodiments described here are only used to explain the present invention and are not intended to limit the present invention.

In order to make the description of the disclosed content more detailed and complete, the following provides illustrative descriptions of the embodiments and specific examples of the present invention, but this is not the only form of implementing or applying specific embodiments of the present invention. The embodiments cover the features of multiple specific examples, as well as the method steps and sequence used to construct and operate these specific examples. However, other specific examples can also be utilized to achieve the same or equal functionality and sequence of steps.

As shown in FIGURE, the upper limb rehabilitation device for sarcopenia includes an outer surface 1, filling material 2, and a keel 3.

The shape of the outer surface is shuttle shaped, the keel is made of rubber material, the filling material is between the keel and the outer surface, including sponge particles and wormwood particles, and hand acupoint protrusion particles are set on the outer surface.

In the present invention the shape of the outer surface is shuttle shaped, the keel is made of rubber material, and the filling material is between the keel and the outer surface, including sponge particles and wormwood particles, which is less likely to cause harm to patients, more suitable for people with weaker strength, can encourage to exercise combined with fun, and can significantly improve the upper limb muscle function of sarcopenia patients. At the same time, it can also have a massage effect on hand acupoints, and because it contains the Chinese herbal medicine of wormwood, it can promote blood circulation, remove blood stasis, dispel dampness and help sleep.

Preferably, a mixing ratio of the sponge particles and wormwood particles is 9:1. At this mixing ratio, it can not only exert the medicinal functions of promoting blood circulation, removing blood stasis, dispelling dampness and aiding sleep of wormwood particles, but also avoid the discomfort of hand grasping caused by the large amount of wormwood particles.

Preferably, the keel includes several transverse and longitudinal spinous processes 4, with adjacent transverse and longitudinal spinous processes connected in the transverse direction. It is precisely by using the structure of the spinous process that the acupoints on the hand receive better massage through its tip.

Preferably, the transverse and longitudinal spinous process includes a transverse portion 41 and a longitudinal portion 42, with the length of the transverse portion being longer than that of the longitudinal portion. This is to match the shuttle shaped structure of the outer surface, so that the outer surface of the entire device is uniformly supported.

Preferably, a vertical distance from the tip of the longitudinal portion to the transverse portion is a half of a vertical distance from the outer surface to the transverse portion. This is the best ratio obtained through many experiments, which allows the hands to be massaged better.

Preferably, the material of the outer surface is poplin, which can make the touch soft and smooth, and add comfort to patients.

An application method for the upper limb rehabilitation device for sarcopenia is also provided, which includes the following steps:

(1) placing two hands at the location of the hand acupoint protrusion particles;
(2) grasping the upper limb rehabilitation device for sarcopenia hard with the hands, so that the keel is close to the hand acupoint protrusion particles;
(3) releasing the hands and restoring the upper limb rehabilitation device for sarcopenia to its original state under the action of sponge particles;
(4) repeating step (1)-(3) repeatedly until a rehabilitation plan is reached.

Although the present invention has a simple structure, it was developed over a long period of time and continuously tested and improved by the inventors. It is not easy to come up with and has extremely broad application prospects in the care and rehabilitation of patients with weak upper limb strength.

The above contents are only the preferable embodiments of the present invention, and do not limit the present invention in any manner. Any improvements, amendments and alternative changes made to the above embodiments according to the technical spirit of the present invention shall fall within the claimed scope of the present invention.

What is claimed is:

1. An upper limb rehabilitation device for sarcopenia, comprising:
   an outer surface, a filling material, a keel,
   wherein a shape of the outer surface is fusiform shaped, the keel is made of rubber material, the filling material is between the keel and the outer surface, the filling material comprises sponge particles and wormwood particles, and hand acupoint protrusion particles are set on the outer surface;
   a mixing ratio of the sponge particles and the wormwood particles is 9:1; and
   the keel comprises a plurality of transverse and longitudinal spinous processes, with adjacent transverse and longitudinal spinous processes connected in a transverse direction.

2. The upper limb rehabilitation device for sarcopenia according to claim 1, wherein each of the plurality of transverse and longitudinal spinous processes comprises a transverse portion and a longitudinal portion, wherein a length of the transverse portion is longer than a length of the longitudinal portion.

3. The upper limb rehabilitation device for sarcopenia according to claim 1, wherein a material of the outer surface is poplin.

4. A method of using the upper limb rehabilitation device for sarcopenia according to claim 3, comprising the following steps:
   (1) placing two hands at the hand acupoint protrusion particles;
   (2) grasping the upper limb rehabilitation device for sarcopenia hard with the two hands, wherein the keel is adjacent to the hand acupoint protrusion particles;
   (3) releasing the two hands and restoring the upper limb rehabilitation device for sarcopenia to an original state under an action of the sponge particles; and
   (4) repeating step (1) to step (3) repeatedly until a rehabilitation plan is reached.

* * * * *